United States Patent
Leonhardt et al.

(10) Patent No.: US 6,803,567 B2
(45) Date of Patent: Oct. 12, 2004

(54) ION MOBILITY SPECTROMETER WITH GC COLUMN AND INTERNAL CONTROLLED GAS CIRCULATION

(75) Inventors: Jürgen Leonhardt, Berlin (DE); Bensch Holger, Berlin (DE); Joachim Franke, Berlin (DE); Rolf Rudolph, Berlin (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 10/602,812

(22) Filed: Jun. 24, 2003

(65) Prior Publication Data

US 2004/0031919 A1 Feb. 19, 2004

(30) Foreign Application Priority Data

Jun. 24, 2002 (DE) ......................... 102 28 912

(51) Int. Cl.[7] ..................... H01J 49/04; G01N 30/64
(52) U.S. Cl. ..................... 250/288; 250/287; 73/23.41; 73/23.42
(58) Field of Search ................ 250/288, 287; 73/23.41, 23.42

(56) References Cited

U.S. PATENT DOCUMENTS

| | | | | |
|---|---|---|---|---|
| 5,457,316 A | * | 10/1995 | Cohen et al. | 250/288 |
| 6,481,263 B1 | * | 11/2002 | Haley et al. | 73/23.41 |

FOREIGN PATENT DOCUMENTS

DE 198 56 784 A1 6/2000

* cited by examiner

Primary Examiner—Jack I. Berman
(74) Attorney, Agent, or Firm—McGlew and Tuttle, P.C.

(57) ABSTRACT

An ion mobility spectrometer with a GC column and an internal circulation system is provided which can be used in trace gas analysis. Due to the special design of the gas circulation, the parameters: carrier gas velocity in the GC column, the flow rate of the gas to be analyzed and the flow rate of the drift gas can be varied extensively independently and without reaction. Additional pumps and gas splitters are arranged in the circulation system for this purpose.

9 Claims, 3 Drawing Sheets

ION MOBILITY SPECTROMETER WITH GC COLUMN AND INTERNAL CONTROLLED GAS CIRCULATION

FIELD OF THE INVENTION

The present invention pertains to an ion mobility spectrometer (IMS) with gas chromatography (GC) column (GC-IMS) and internal controlled gas circulation, which can be used in trace gas analysis.

BACKGROUND OF THE INVENTION

A gas analyzer with internal gas circulation has been known from DE-OS 198 56 784. A circulation filter for water vapor and higher-molecular-weight constituents of the gas, a circulating pump, a metering means for the inlet for the gas to be analyzed as well as a gas-chromatographic separation column to a closed circulation system are additionally arranged in a gas circulation of a concentration-dependent gas detector. The air of the internal gas circulation is used as the carrier gas utilizing the separation column of a suitable low admission pressure to distinguish components with equal mobility but different retention time and to suppress cross sensitivities. The supply of an external carrier gas can be eliminated.

However, many measurement problems in industrial practice require defined analysis times in agreement with technological requirements such as the rhythm of the measurement, the accuracy of the measurement and the sensitivity of the measurement.

SUMMARY OF THE INVENTION

According to the invention an ion mobility spectrometer with GC column and internal controlled gas circulation is provided. A flow of gas to be analyzed from a sample gas outlet of the IMS cell is split via a splitter into two partial flows. One branch has a pump and a analytical circulation filter. The smaller partial flow is sent to a sample gas inlet of the IMS cell via a switchable sample loop device for passing on or sampling and subsequently via a GC column. The larger flow of the gas to be analyzed is sent back from a splitter to a branch with a further pump, a circulation filter to an additional gas inlet of the IMS cell. An additional gas outlet of the IMS cell provides the flow back to the further pump as well as a pressure sensor and a temperature sensor of the larger flow gas circulation. This circulating gas flow is split internally in the IMS cell in a splitter into a drift gas flow and the internal flow of the gas to be analyzed.

The circulating flow may be split via a splitter arranged outside the IMS cell into the drift gas flow, which is sent into the cell via the inlet, and the flow of gas to be analyzed, which is sent to the branch.

The Ion mobility spectrometer may be provided that a splitter is provided in the flow of gas to be analyzed. A partial flow may be sent as a make-up gas flow via another splitter to the carrier gas flow. This partial flow is used for diluting the sample.

The invention makes possible the independent control of defined analysis times in agreement with technological requirements such as the rhythm of the measurement, the accuracy of the measurement and the sensitivity of the measurement in the embodiment of an analysis system operating with a closed gas circulation. The gas flow to be analyzed, which leaves the IMS cell, is sent over an additional pump and an additional filter. The gas flow to be analyzed is split downstream of the additional pump and an additional filter into two partial flows.

The larger partial flow is returned in a closed circuit to the area upstream of the pump. The other partial flow is sent via the sample loop (in the solenoid valve (MV) block) to the GC column and then to the sample inlet of the IMS cell. It is ensured as a result that the admission pressure before the GC column can be set sensitively and varied by varying the output of the pump. Disturbing pump shocks are eliminated by the filter. The splitting of the gas flow is provided because the GC column is able to process, in principle, only very small gas flows and a sensitive control based on the output of the pump is possible at relatively large flows only.

At the same time, the additional possibility of controlling the admission pressure of the GC column ensures the absence of reaction of the gas flow to be analyzed on the closed drift gas system that is formed by the circulating pump, the circulating pump filter, the drift gas inlet of the IMS cell and the drift gas outlet of the IMS cell, and the independence of a variation of the gas flow to be analyzed. The parameters in this circulation can also be varied based on the output of the circulating pump independently from reactions on the circulation of the gas to be analyzed. Sensors for the pressure and temperature provide data used for the control of the circulation parameters and the compensation of the measured values of the IMS detection by calculation. These sensors may be additionally arranged in the drift gas circulation.

In particular, the following parameters and properties can be varied independently from one another due to this arrangement:

| | |
|---|---|
| Velocity of the carrier gas in the GC column: | time response of the arrangement |
| Flow rate of the gas to be analyzed, which enters the IMS cell: | sensitivity |
| Flow rate of the drift gas: | accuracy, resolution |

The present invention shall be described in greater detail below. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
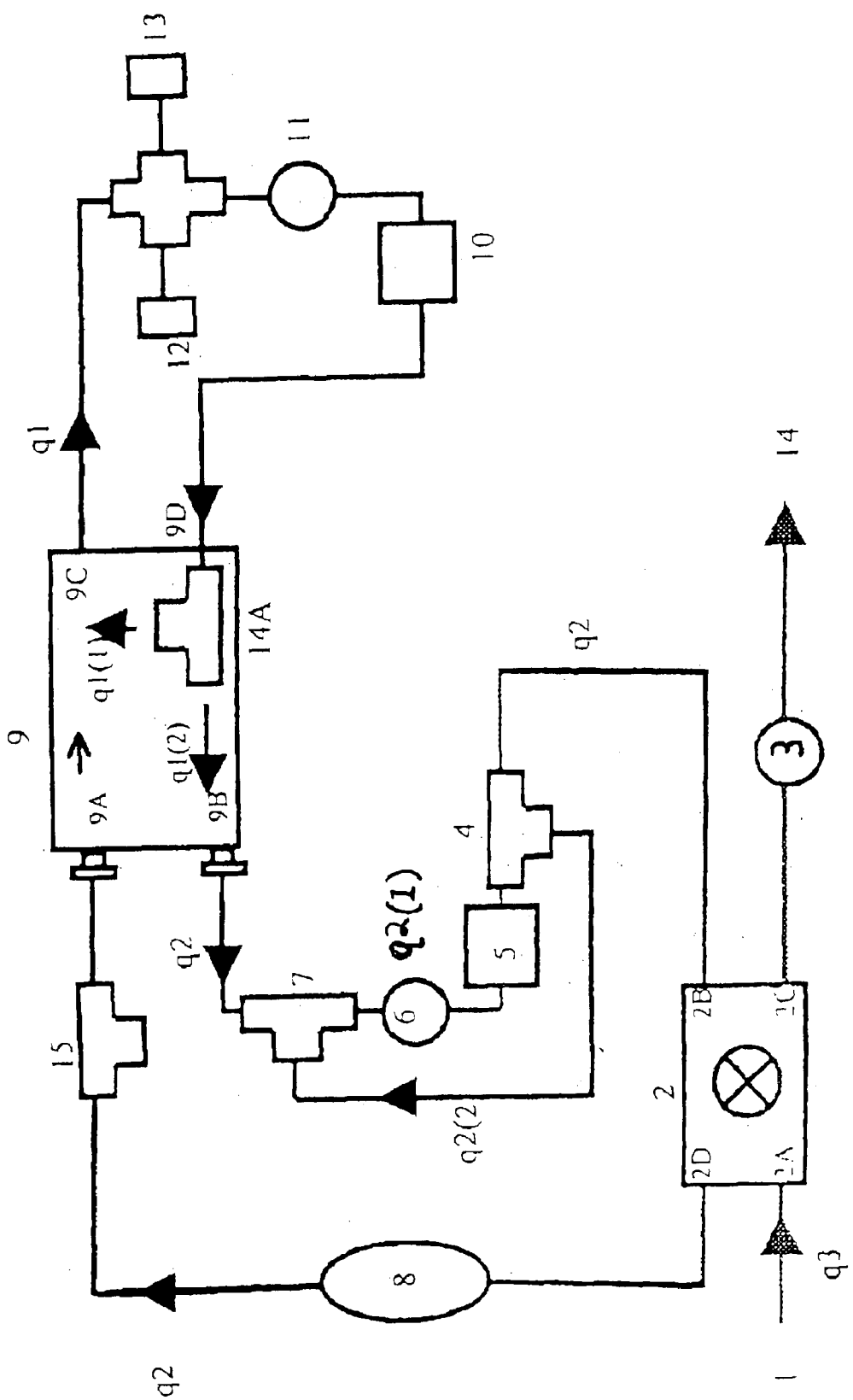
FIG. 1 is a diagram showing an exemplary embodiment of the device according to the present invention with a gas splitter arranged within the IMS cell.

Referring to the drawings in particular, the invention comprises an ion mobility spectrometer with GC column and internal controlled gas circulation. These embodiments of the invention are shown in FIGS. 1, 2 and 3.

The embodiment of FIG. 1 includes a MV block 2. This has a normal segment from inlet 1 via the sample loop portion 2A to 2C and pump 3 to the outlet 14. This may be switched over so that the sample volume located in the region between 2A and 2C is transferred in between 2D and 2B with the portion between 2D and 2B thereby providing a sample for analysis. The embodiment of FIG. 1 also includes a GC column 8 and an IMS cell 9. The cell 9 has an inlet 9A, an outlet 9B, an outlet 9C and an inlet 9D. In the embodiment of FIG. 1 the outlet 9C is connected back to the inlet 9D through the circulation pump 11 and circulation filter 10. Pressure sensor 12 and a temperature sensor 13 are operatively connected to the gas flow q1. In the embodiment of FIG. 1 the IMS cell 9 includes an IMS cell splitter 14A which splits the incoming flow from 9D q1 into two portions q1(1) and q1(2). The flow q1(2) exits exit 9B as to flow q2. The branch of the circuit with flow q2 includes a branch element 7 feeding the flow q2 through additional pump 6 and additional filter 5 to splitter 4. By means of pump 6 including filter 5 and splitters 4 and 7 a pressure increase is realized thus providing a suitable flow q2 through GC-column 8.

Figure 2:
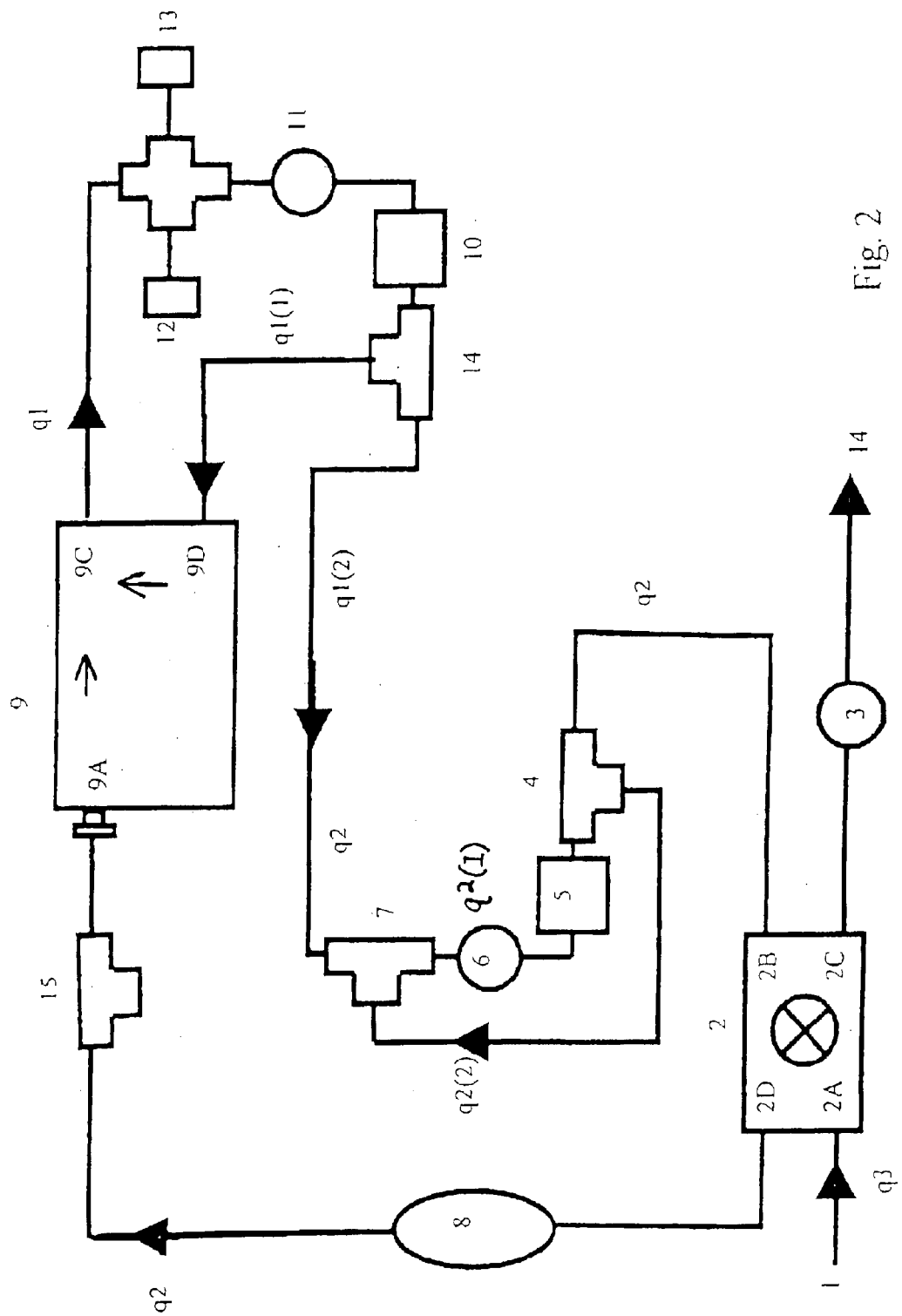
FIG. 2 is a diagram showing an exemplary embodiment of the device according to the present invention with a gas splitter arranged outside the IMS cell.

The embodiment of FIG. 2 is similar to the embodiment of FIG. 1. The portion of the circuit or loop with flow q2 proceeds in a manner similar to that of the embodiment of FIG. 1. However, unlike the embodiment of FIG. 1 the flow q1 is directed to a splitter 14 which is external of the IMS cell 9. Splitter 14 breaks the flow q1 into the flow q1(1) which proceeds back to the IMS cell 9 via inlet 9D. The other branch of splitter 14 forms flow q1(2) which proceeds as flow q2 as described above.

Figure 3:
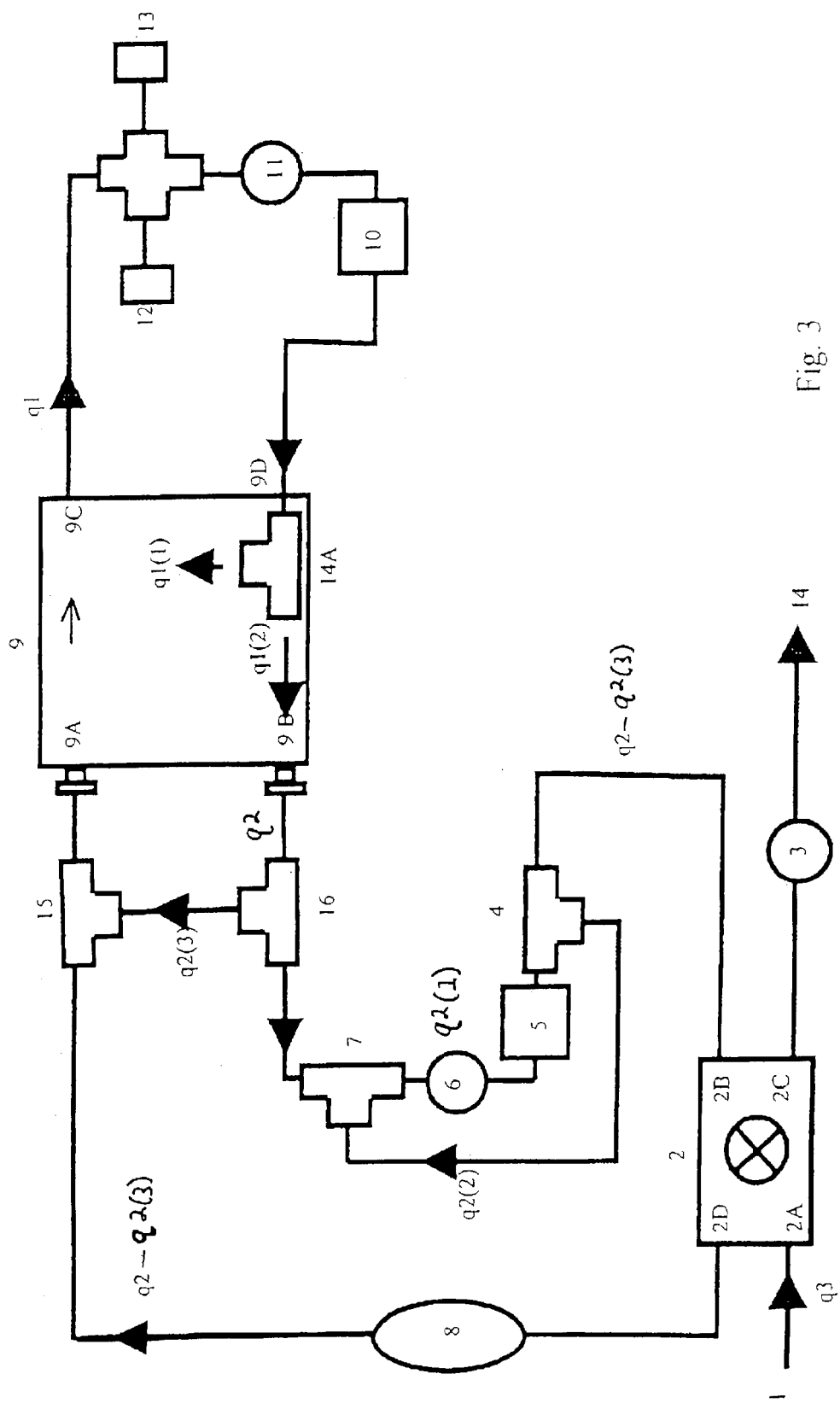
FIG. 3 is a diagram showing an exemplary embodiment of the device according to the present invention with a gas splitter arranged within the IMS cell and with a splitter in the flow of gas to be analyzed splitting a partial flow used for diluting the sample.

The embodiment of FIG. 3 is identical to the embodiment of FIG. 1 except an additional splitter 16 is provided which is connected to the outlet 9B of the IMS cell 9. This splitter 16 branches off a partial flow q2(3) from flow q2 which is sent as a make-up gas flow via branch element 15 to provide a make-up gas flow which is used for diluting the sample.

In the stand-by mode, the sample gas flow q3 is delivered from the inlet 1 via the sample loop (2A to 2C) in the MV block 2 and the pump 3 to the outlet 14. Sampling is not performed. The apparatus operates in a circulation mode circulating around flow portions q2(1), q1, q2 and purifies itself.

The connection 2B–2D is in parallel to the connection 2A–2C within the MV block 2. The MV block 2 is briefly switched over with the portion (loop) between 2B–2D and the portion (sample loop) between 2A–2C switching positions for the sampling and the start of a measurement cycle. The sample volume located in the sample loop between 2A and 2C is moved to the location between 2D and 2B upon switching. The sample volume is conveyed in the circulation in the carrier gas flow q2(1) to the GC column 8. At the GC column 8 a preliminary gas-chromatographic separation of the constituents of the sample takes place according to their different retention times.

After the sample has been introduced into the circulation system, the MV block 2 is immediately reset to the connection configurations 2A–2C and 2B–2D.

The preliminarily separated sample volume is conveyed farther to the sample inlet 9A of the IMS cell 9. The ion mobility spectrometric analysis of the constituents of the sample is performed at the IMS cell 9. The analytical circulation q2 is completed via the sample outlet 9B of the IMS cell 9, the branch (flow combiner) 7, the pump 6, the filter 5 and the splitter 4 for the gas to be analyzed. The gas flow q2 for the gas to be analyzed is split in the splitter 4 into the two components. The carrier gas flow q2(1) is directed to the MV block 2 and the bypass flow q2(2) back to the branch 7. The circulation q2 of the gas to be analyzed can be controlled on the basis of the output of the pump 6. At the same time, the bypass flow q2(2) ensures the necessary pump load for the pump 6, which would not be guaranteed by the carrier gas flow q2(1) alone.

The basic circulation with the circulating gas flow q1 is formed by the pump 11, the circulation filter 10, the inlet 9D and the gas outlet 9C of the IMS cell 9. This basic circulation is controlled by the output of the pump 11 on the basis of the parameters from the sensors arranged in the circulation, namely, the pressure sensor 12 and the temperature sensor 13 without reaction on the analysis circulation q2.

In the embodiments of FIGS. 1 and 3 the splitting of the circulating gas q1 is performed internally in a cell splitter 14A. The cell splitter 14A splits the flow q1 into the drift gas flow q1(1) and the flow q1(2) of the gas to be analyzed. In the embodiment of FIGS. 1 and 2 the flow q1(2) is equal to the flow q2 of the gas to be analyzed.

This arrangement of FIG. 1 ensures that the flows can be varied very extensively independently from one another in both the circulating gas flow q1 and the flow q2 of the gas to be analyzed.

According to the embodiment of FIG. 2, the splitting of the circulating gas flow into the drift gas flow q1(1) and the gas flow to be analyzed q1(2), q2 may also take place in an externally arranged splitter 14. Splitter 14 directs drift gas flow q1(1) to inlet 9D and gas flow to be analyzed q1(2), q2 to branch 7.

According to the embodiment of FIG. 3 an additional splitter 16 is provided receiving gas flow to be analyzed q1(2). The additional splitter 16 branches off parts of the gas to be analyzed q1(2) to form diluting gas flow q2(3). Diluting gas flow q2(3) mixes with the carrier gas flow q2(1) for diluting the sample by additional branch (flow combiner) 15 arranged in the flow q1(2), q2 of the gas to be analyzed in FIG. 3.

While specific embodiments of the invention have been shown and described in detail to illustrate the application of the principles of the invention, it will be understood that the invention may be embodied otherwise without departing from such principles.

What is claimed is:

1. An ion mobility spectrometer, comprising:
    a switchable sample loop device;
    an ion mobility spectrometer (IMS) cell with a sample gas inlet and a sample gas outlet;
    a circulation pump;
    a circulation filter;
    an analytical circulation pump;
    an analytical circulation filter;
    a gas chromatography (GC) column; and
    a flow path defining an internal controlled gas circulation with a gas flow to be analyzed from the sample gas outlet of the IMS cell to the circulation pump, circulation filter, analytical circulation pump and analytical circulation filter and branching into two partial flows with a smaller partial flow sent via said switchable sample loop device for passing the flow on or providing a sampling and subsequently via said GC column to said sample gas and with a larger partial flow of the gas to be analyzed sent back to just upstream of said analytical circulation pump and analytical circulation filter, and a pressure sensor and a temperature sensor in functional connection with said internal controlled gas circulation.

2. An ion mobility spectrometer in accordance with claim 1, further comprising a gas splitter internally in the IMS cell for splitting gas flow between a drift gas flow and the flow of the gas to be analyzed, wherein said IMS cell has an additional gas inlet and an additional gas outlet, with said circulation pump, said circulation filter, said pressure sensor and said temperature sensor being arranged in a gas circulation loop between said additional gas outlet and said additional gas inlet.

3. An ion mobility spectrometer in accordance with claim 1, further comprising a gas splitter, arranged outside the IMS cell, for splitting gas flow into a drift gas flow q1 sent into the cell via another IMS cell inlet and the flow of gas to be analyzed.

4. An ion mobility spectrometer in accordance with claim 1, further comprising a splitter in the flow of gas to be analyzed to form a partial diluting flow for diluting the sample and a remaining flow of gas to be analyzed.

5. A method of using an ion mobility spectrometer with a switchable sample loop device comprising an ion mobility spectrometer (IMS) cell with a sample gas inlet and a sample gas outlet, a circulation pump, a circulation filter, an analytical circulation pump, an analytical circulation filter, a gas chromatography (GC) column and a flow path defining an internal controlled gas, the method comprising:

directing a gas flow to be analyzed to leave the IMS cell via the analytical circulation pump and analytical filter;

splitting the gas flow to be analyzed downstream of the analytical circulation pump and analytical circulation filter into two partial flows with the larger partial flow returned in a closed circuit to the area upstream of the analytical circulation pump and with the other partial flow sent via the switchable sample loop device to the GC column and then to the sample inlet of the IMS cell.

6. An ion mobility spectrometer system, comprising:

a switchable sample loop device;

an ion mobility spectrometer (IMS) cell with a sample gas inlet and a sample gas outlet;

a circulation pump;

a circulation filter;

an analytical circulation pump;

an analytical circulation filter;

a gas chromatography (GC) column;

a sampling gas flow of a gas to be sampled;

a solenoid valve through which said sampling gas flow passes; and a flow path defining an internal controlled gas circulation with a gas flow to be analyzed from the sample gas outlet of the IMS cell to the circulation pump, circulation filter, analytical circulation pump and analytical circulation filter and branching into two partial flows with a smaller partial flow sent via said switchable sample loop device for passing the flow on or providing a sampling and subsequently via said GC column to said sample gas and with a larger partial flow of the gas to be analyzed sent back to just upstream of said analytical circulation pump and analytical circulation filter, and a pressure sensor and a temperature sensor in functional connection with said internal controlled gas circulation, said system at any particular time operating in one of:

i) a stand-by mode wherein said solenoid valve allows said sampling gas flow to pass through said solenoid valve without diversion, and gas involved in said internal controlled gas circulation is purified by said circulation filter and said analytical circulation filter;

ii) a sample acquisition mode in which said solenoid valve captures a sample of the sample gas to be sampled from the sample gas flow and transfers said sample to said internal controlled gas circulation introducing said sample to said internal controlled gas circulation; and iii) an analysis mode wherein the sample introduced in the sample acquisition mode is analyzed.

7. An ion mobility spectrometer system in accordance with claim 6, further comprising a gas splitter internally in the IMS cell for splitting gas flow between a drift gas flow and the flow of the gas to be analyzed, wherein said IMS cell has an additional gas inlet and an additional gas outlet with said circulation pump, said circulation filter, said pressure sensor and said temperature sensor being arranged in a gas circulation loop between said additional gas outlet and said additional gas inlet.

8. An ion mobility spectrometer system in accordance with claim 6, further comprising a gas splitter, arranged outside the IMS cell, for splitting gas flow into a drift gas flow q1 sent into the cell via another IMS cell inlet and the flow of gas to be analyzed.

9. An ion mobility spectrometer system in accordance with claim 6, further comprising a splitter in the flow of gas to be analyzed to form a partial diluting flow for diluting the sample and a remaining flow of gas to be analyzed.

* * * * *